United States Patent [19]

Green

[11] Patent Number: 4,508,253
[45] Date of Patent: Apr. 2, 1985

[54] SURGICAL FASTENER APPLYING APPARATUS

[75] Inventor: David T. Green, Norwalk, Conn.

[73] Assignee: United States Surgical Corporation, Norwalk, Conn.

[21] Appl. No.: 538,931

[22] Filed: Oct. 4, 1983

[51] Int. Cl.³ .............................................. A61B 17/04
[52] U.S. Cl. ................... 227/19; 128/334 R; 227/135; 227/DIG. 1; 227/120
[58] Field of Search ............ 128/334 R; 227/DIG. 1, 227/19, 120, 136, 137, 135, 156

[56] References Cited

U.S. PATENT DOCUMENTS

| | | | |
|---|---|---|---|
| 3,080,564 | 3/1963 | Strekopitov et al. | 227/DIG. 1 |
| 3,269,630 | 8/1966 | Fleischer | 227/107 |
| 3,275,211 | 9/1966 | Hirsch et al. | 227/124 |
| 3,315,863 | 4/1967 | O'Dea | 227/19 |
| 3,494,533 | 2/1970 | Green et al. | 227/19 |
| 3,589,589 | 6/1971 | Akopov | 227/153 |
| 3,692,224 | 9/1972 | Astafiev et al. | 227/19 |
| 3,935,981 | 2/1976 | Akopov et al. | 227/19 |
| 3,949,923 | 4/1976 | Akopov et al. | 227/19 |
| 4,241,861 | 12/1980 | Fleischer | 227/135 |
| 4,296,881 | 10/1981 | Lee | 227/30 |
| 4,305,539 | 12/1981 | Korolkov et al. | 227/8 |
| 4,351,466 | 9/1982 | Noiles | 227/8 |
| 4,354,628 | 10/1982 | Green | 227/19 |
| 4,383,634 | 5/1983 | Green | 227/19 |
| 4,402,444 | 9/1983 | Green | 227/19 |

FOREIGN PATENT DOCUMENTS

| | | |
|---|---|---|
| 906791 | 9/1962 | United Kingdom . |
| 913218 | 12/1982 | United Kingdom . |
| 747469 | 7/1980 | U.S.S.R. ................ 227/19 |

Primary Examiner—Paul A. Bell
Attorney, Agent, or Firm—Robert R. Jackson; John E. Nathan

[57] ABSTRACT

Surgical fastener applying apparatus including an actuator and a removable surgical fastener container cartridge. The cartridge fits loosely into a cartridge holder part of the actuator which translates linearly toward or away from an anvil part of the actuator. As the cartridge holder translates toward the anvil, the cartridge is automatically brought into alignment and registration with the anvil.

19 Claims, 13 Drawing Figures

SURGICAL FASTENER APPLYING APPARATUS

FIELD OF THE INVENTION

This invention relates to apparatus for applying surgical fasteners such as metal surgical staples. More particularly, the invention relates to surgical fastener applying apparatus of the type which includes an actuator for removably receiving a fastener containing cartridge.

BACKGROUND OF THE INVENTION

There are several types of known surgical fastener applying devices which comprise an actuator for removably receiving a fastener containing cartridge. One such device is shown in Hirsch et al. U.S. Pat. No. 3,275,211. In the Hirsch et al. device, a cartridge containing a plurality of surgical staples fits snugly into a cartridge holder element of the actuator. The cartridge holder element reciprocates linearly toward or away from an anvil portion of the actuator by operation of a first actuator control element (i.e., a rotating knob or wing nut). In particular, the tissue to be fastened is clamped between the cartridge and the anvil by reciprocating the cartridge holder element (and therefore the cartridge) toward the anvil. The staples are driven from the cartridge and part way through the clamped tissue by operation of a second actuator control element (i.e., a pivoting handle). The ends of the staple legs are crimped or clinched by contact with the anvil.

The Hirsch et al. device has many desirable features, but satisfactory operation of that device depends on accurate alignment between the cartridge and the anvil in order to assure that all of the staple legs enter the staple clinching pockets in the anvil for proper clinching by the anvil. Thus the cartridge must fit snugly in the cartridge holder element, and the cartridge holder element must be precisely aligned with the anvil, while at the same time being movable relative to the anvil and capable of resisting the large tissue clamping and staple clinching forces which tend to drive the staple holder and anvil apart.

Some of the requirements of the Hirsch et al. device are alleviated by devices of the type shown in Green U.S. Pat. No. 4,383,634. In the Green device the staple holder, anvil, and alignment pin are all connected together in a single disposable unit. In addition, the alignment pin operates automatically when the actuator is operated. The elements which provide the necessary precise alignment between the staple holder and anvil are also all confined to the cartridge assembly, thereby greatly simplifying and reducing the cost of the actuator. However, in the Green device the staple holder and anvil are pivotally connected to one another (although limited translational motion of these elements is also possible). Some users prefer the purely linear reciprocation of the staple holder relative to the anvil which is characteristic of the Hirsch et al. device.

In view of the foregoing, it is an object of this invention to improve and simplify surgical fastener applying apparatus of the type described above.

It is a more particular object of this invention to provide surgical fastener applying apparatus which combines the relatively low cost construction and simplified operation of the above-mentioned Green device with the linear relative motion of the staple holder and anvil in the above-mentioned Hirsch et al. device.

SUMMARY OF THE INVENTION

These and other objects of the invention are accomplished in accordance with the principles of the invention by providing a staple holding cartridge which drops relatively loosely into a cartridge holder part of an actuator. The cartridge drops into the cartridge holder at an angle relative to the anvil, and means are provided for urging the cartridge into substantial parallelism with the anvil after the cartridge is in the holder. Means are also provided for retaining the cartridge in the holder when the cartridge is substantially parallel to the anvil.

The cartridge holder reciprocates linearly relative to the anvil. One end of the staple holding cartridge is aligned relative to the anvil by means of a rail and channel connection between the cartridge and the actuator member which terminates in the anvil. Reciprocation of the cartridge holder toward the anvil automatically forces the cartridge into parallel alignment with the anvil. As the cartridge becomes parallel to the anvil, means associated with the cartridge and cartridge holder force the elements of the rail and channel connection together, thereby assuring proper registration of the cartridge with the anvil in a direction parallel to the longitudinal axis of the anvil.

The cartridge also includes an alignment pin adjacent the end remote from the rail and channel connection. When the cartridge holder is reciprocated toward the anvil, the alignment pin automatically extends from the cartridge into the anvil, thereby assuring proper alignment of the end of the cartridge and anvil remote from the rail and channel connection.

Further features of the invention, its nature and various advantages will be more apparent from the accompanying drawing and the following detailed description of the invention.

DETAILED DESCRIPTION OF THE INVENTION

Figure 1:
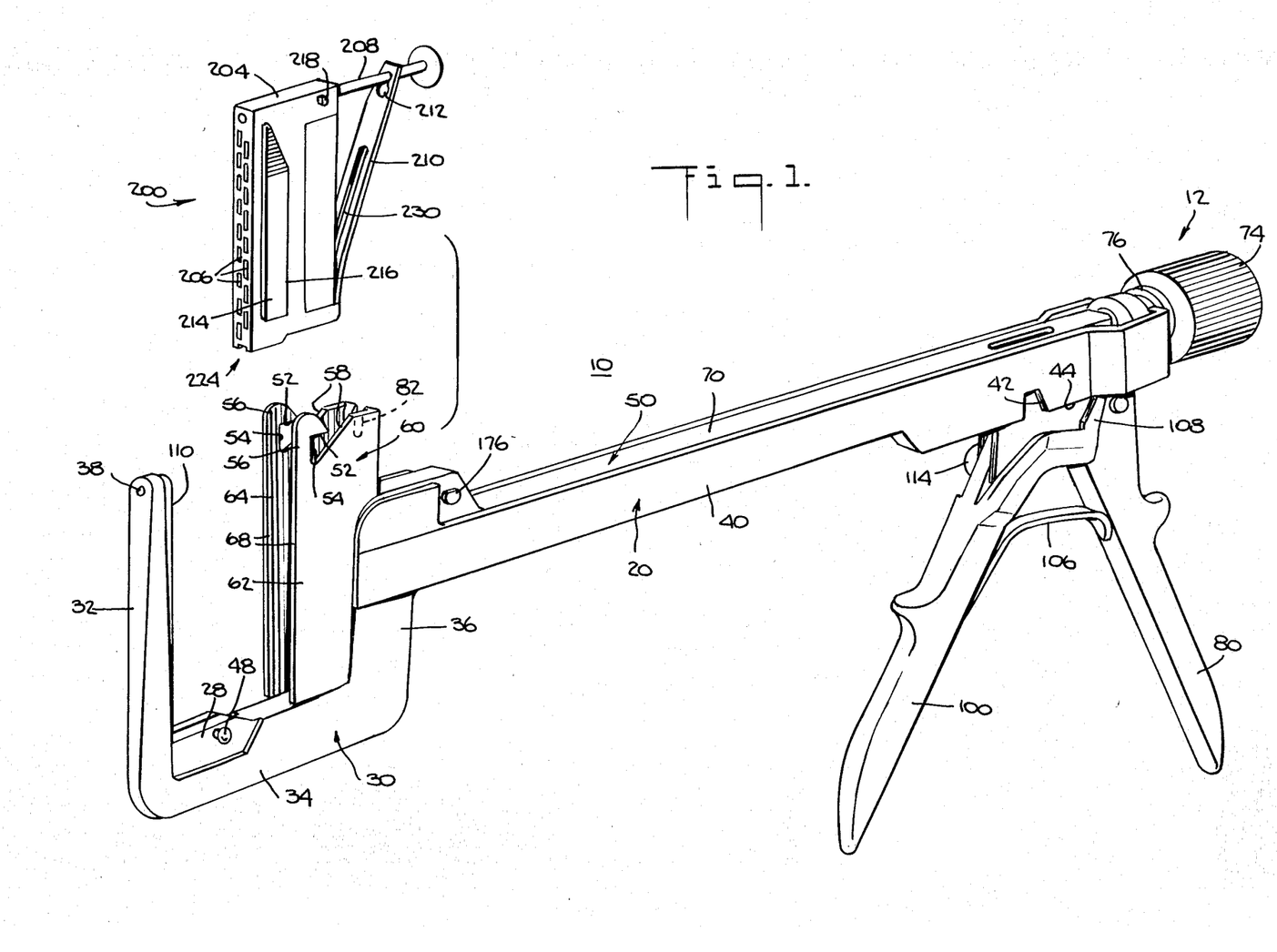
FIG. 1 is a perspective view of an illustrative embodiment of the invention showing the fastener holding cartridge and the cartridge actuator separate from one another.

As can be seen in FIG. 1, the two principal components of the surgical fastener applying apparatus 10 of this invention are actuator assembly 12 and surgical fastener containing cartridge 200. Cartridge 200 is removably receivable in actuator 12 as described in detail below. When cartridge 200 is disposed in actuator 12, actuator 12 is operated as described in detail below to drive the surgical fasteners contained in cartridge 200 at least part way through body tissue placed in the instrument in order to fasten the tissue. Cartridge 200 is typically disposable after a single use in order to avoid all difficulty, time, and expense which would otherwise be required to clean, sterilize, and reload the cartridge for reuse. Actuator 12, on the other hand, is typically reusable or "permanent". Of course, cartridge 200 could be made reusable if desired, and actuator 12 could be made disposable if desired.

Actuator 12 includes a frame 20 having a distal U-shaped portion 30 and a proximal longitudinal shaft portion 40. Distal U-shaped frame portion 30 includes a distal leg 32, a base 34, and a proximal leg 36. The longitudinal axes of elements 32, 34, and 36 define a plane (the plane of the paper in FIG. 2) which is sometimes referred to herein as the plane defined by the U. The longitudinal axis of shaft 40 also lies in this plane.

Figure 3:
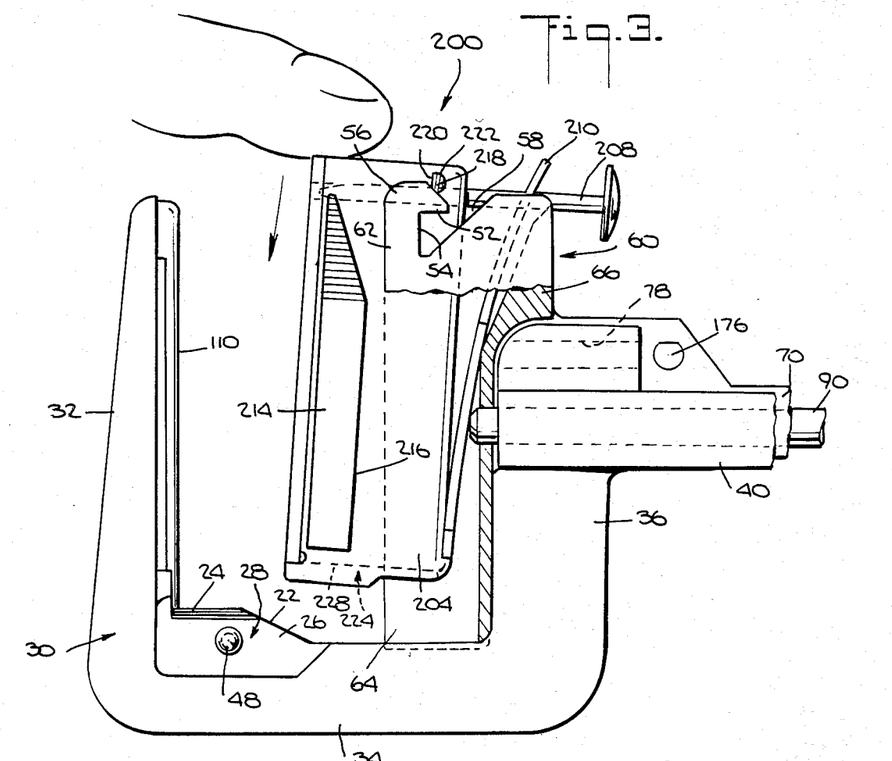
FIG. 3 is a partly sectional elevational view of a part of the apparatus of FIG. 1 showing a later stage in the operation of that apparatus.

Shaft 40 is a channel-shaped member which opens upwardly as viewed in FIG. 1. Mounted for longitudinal reciprocation in shaft 40 is clamp actuator assembly 50. Clamp actuator assembly 50 includes distal cartridge holder 60, intermediate longitudinal clamp pusher 70, and proximal handle 80. Cartridge holder 60 is a channel-shaped member disposed in the U-shaped portion 30 of frame 20. The channel-shaped member which comprises cartridge holder 60 includes laterally spaced, parallel side members 62 and 64 connected together by proximal base 66 (FIG. 3). Side members 62 and 64 are substantially parallel to the plane defined by the U. The longitudinal axis of the channel defined by cartridge holder 60 is substantially parallel to the distal leg 32 of the U. This channel opens in the distal direction and is also open at both of its ends (i.e., the end adjacent base 34 and the opposite end remote from base 34).

Figure 2:
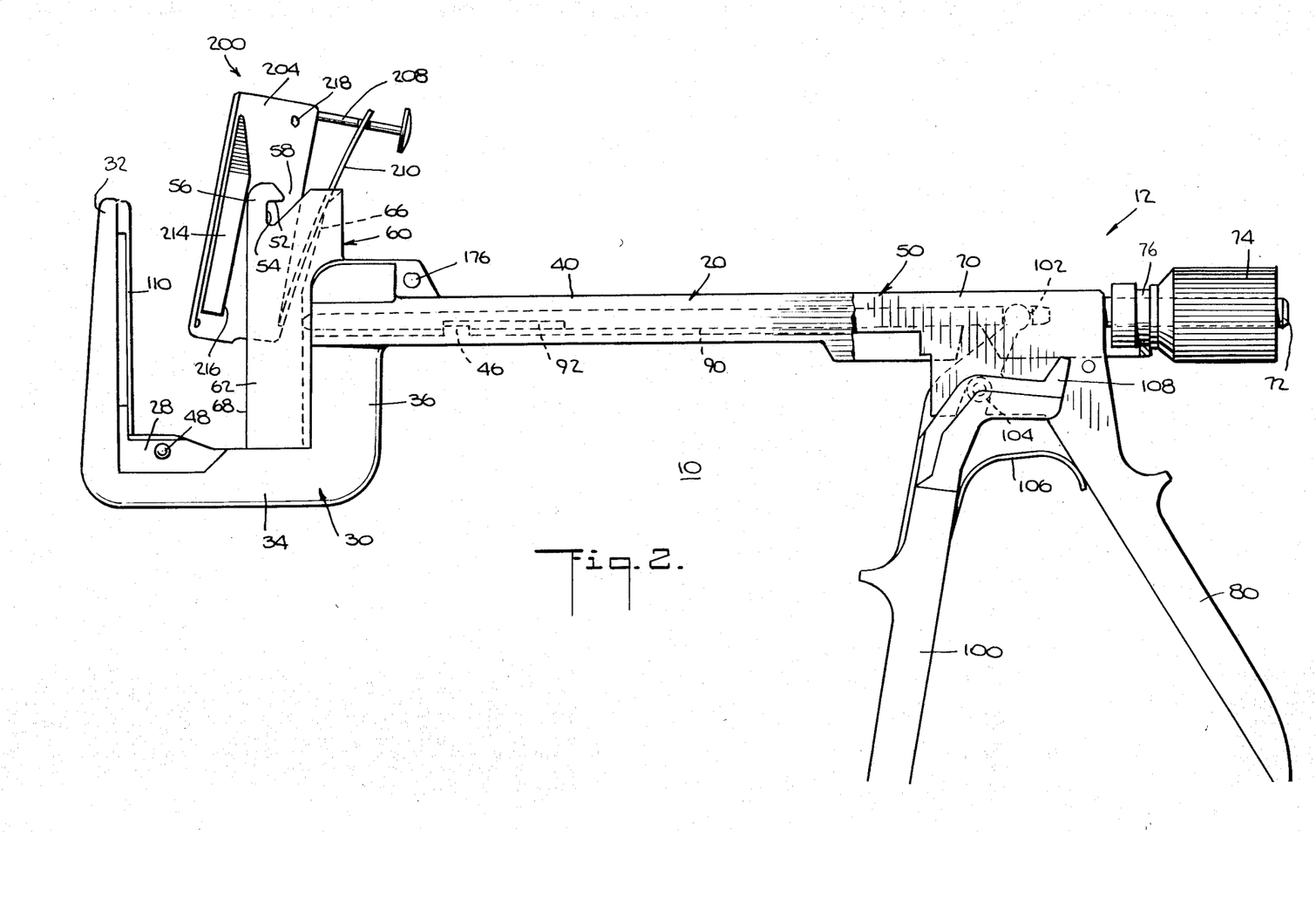
FIG. 2 is a partly sectional elevational view of the apparatus of FIG. 1 showing an early stage in the operation of that apparatus.

Extending from the proximal end of clamp pusher 70 is a threaded stud 72 (FIG. 2). Knurled knob 74 is threadedly mounted on stud 72. The distal shank of knob 74 includes annular recess 76 which is rotatably engaged in a slot in the proximal end of shaft 40. Accordingly, rotation of knob 74 in one direction causes clamp actuator assembly 50 to move distally relative to frame 20, and rotation of knob 74 in the opposite direction causes clamp actuator assembly 50 to move proximally relative to frame 20.

Clamp pusher 70 is also a channel-shaped member which opens downwardly as viewed in FIG. 1. Mounted for longitudinal reciprocation in clamp pusher 70 is fastener pusher 90 (FIGS. 2 and 3). The distal end of fastener pusher 90 communicates with the channel defined by cartridge holder 60. A proximal end portion of fastener pusher 90 receives the upper end portion 102 (FIG. 2) of fastener actuator handle 100. Fastener actuator handle 100 is pivotally connected to clamp pusher assembly 50 by pin 104. Handle 100 is resiliently biased to pivot clockwise about pin 104 as viewed in FIGS. 1 and 2 by leaf spring 106 which is connected to handle 100 at one end and which bears on handle 80 adjacent the other end. When handle 100 is pivoted in the counter-clockwise direction as viewed in FIGS. 1 and 2, fastener pusher 90 moves in the distal direction relative to clamp pusher assembly 50. When handle 100 is released, spring 106 restores handle 100 and fastener pusher 90 to their initial positions relative to clamp pusher assembly 50.

Figure 7:
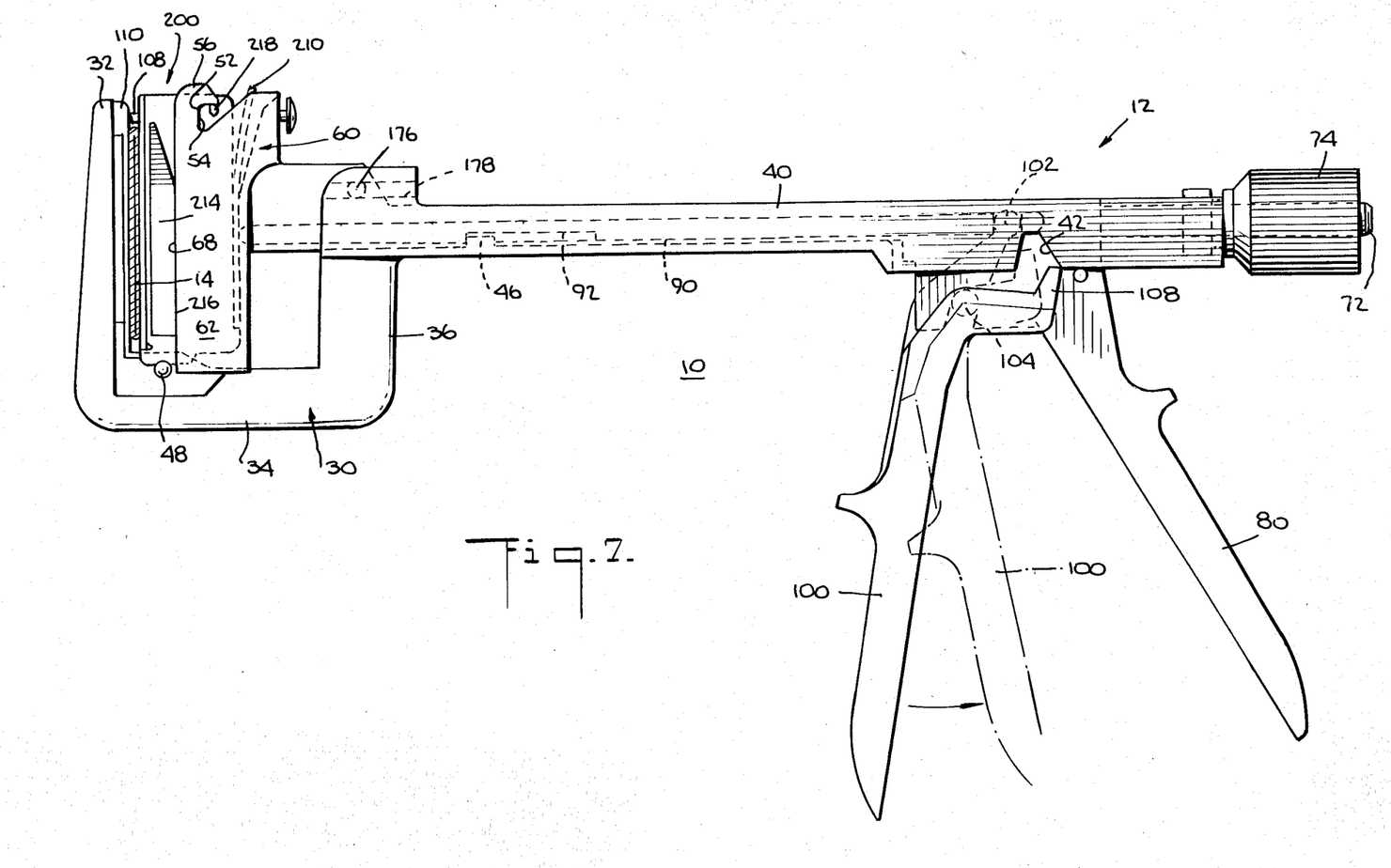
FIG. 7 is a view generally similar to FIG. 2 showing a still later stage in the operation of the apparatus.

Actuator assembly 12 includes a safety interlock which automatically prevents operation of handle 100 until cartridge holder 60 has been reciprocated toward distal leg 32 by at least a predetermined amount. This safety interlock includes projection 108 on handle 100 and notch 42 in shaft 40. When cartridge holder 60 is retracted proximally from leg 32 as shown in FIGS. 1 and 2, the upper end of projection 108 bears on shaft surface 44 which is proximal of notch 42. This prevents handle 100 from being pivoted counter-clockwise as viewed in FIGS. 1 and 2. As knob 74 is rotated to cause cartridge holder 60 to move distally toward leg 32, handle projection 108 similarly moves distally toward notch 42. When cartridge holder 60 is a predetermined distance from leg 32 as shown in FIG. 7, handle projection 108 can enter notch 42 and handle 100 can be pivoted counter-clockwise as shown in broken lines in FIG. 7. Accordingly, fastener pusher 90 cannot be reciprocated in the distal direction by operation of handle 100 until cartridge holder 60 is less than a predetermined maximum distance from leg 32. Because elements 42 and 108 are visible to the operator of the instrument, they also provide a visible proximal indication of whether or not the tissue has been clamped sufficiently for fastening.

In the particular embodiment shown in the drawing, cartridge 200 contains a plurality of U-shaped metal surgical staples 202 (FIG. 8) arranged in two parallel spaced rows. When staples 202 are driven from cartridge 200 as described below, the distal ends of the legs of the staples are clinched or crimped by contact with an anvil member 110 which is mounted on or formed as part of the distal leg 32 of actuator frame 20. Anvil 110 has a plurality of depressions 112 (FIG. 8), each of which receives and clinches the distal end of a respective one of the staple legs. Anvil 110 may be a removable and disposable part of the apparatus.

If desired, two-part plastic surgical fasteners of the general type shown in Noiles U.S. Pat. No. 4,060,089 can be used instead of metal staples. In that event the staple clinching anvil 110 in the embodiment depicted herein would be replaced by a member for supporting the retainer part or parts of the two-part fasteners. The term "surgical fasteners" is used herein as a generic term for metal surgical staples, two-part plastic surgical fasteners, and their equivalents. Similarly, the term "anvil" is used herein as a generic term for the anvil used to clinch metal surgical staples, the retainer support member used with two-part plastic surgical fasteners, and the equivalents of these elements.

Cartridge 200 includes a housing 204 having two parallel rows of staple containing apertures 206 on the distal side of the cartridge. Each aperture 206 contains a U-shaped metal staple 202 oriented so that the free ends of the legs of each staple point in the distal direction. An alignment pin 208 is mounted in cartridge 200 for reciprocal motion in a direction parallel to the longitudinal axis of the pin. When cartridge 200 is properly positioned in cartridge holder 60 as described below, pin 208 is located on the side of cartridge 200 remote from base 34 and the longitudinal axis of pin 208 is substantially parallel to base 34. A leaf spring 210 is mounted on the proximal side of cartridge 200 remote from apertures 206. The lower end of spring 210 is attached to cartridge housing 204. The upper end of spring 210 includes an aperture 212. The proximal end of pin 208 passes through aperture 212 and is captured by spring 210 by means of an annular recess in pin 208.

Cartridge housing 204 has several surface features which cooperate with various parts of actuator 12 to insure proper alignment and registration between cartridge 200 and anvil 110 so that when staples 202 are driven from the cartridge, the free ends of the staple legs enter and are clinched by anvil depressions 112. The term "alignment" is generally used herein to refer to the proper positioning of cartridge 200 relative to anvil 110 in the direction perpendicular to the plane defined by the U. The term "registration" is generally used herein to refer to the proper positioning of cartridge 200 relative to anvil 110 in the direction parallel to the longitudinal axis of anvil 110 or distal frame leg 32. The term "parallelism" is generally used herein to refer to positioning of cartridge 200 so that the distal surface of the cartridge is parallel to anvil 110. The term "parallel alignment" is used herein to refer to concurrent "parallelism" and "alignment" (as those terms are defined above) of cartridge 200 relative to anvil 110.

Figures 11, 12, 13:
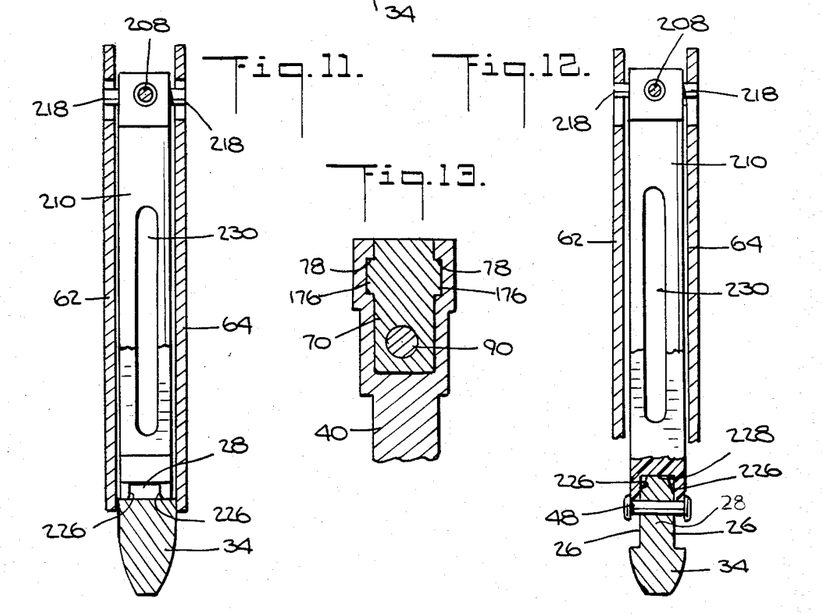
FIG. 11 is a sectional view taken along the line 11—11 in FIG. 4.
FIGS. 12 and 13 are sectional views taken along the lines 12—12 and 13—13, respectively, in FIG. 6.

On each of the two lateral sides of cartridge housing 204 is a raised block 214, only one of which is visible in the Figures. The proximal surface 216 of each raised block 214 is a stop surface which is parallel to the distal surface of cartridge 200. Also on each of the two lateral sides of cartridge housing 204 is a laterally extending lug 218. Lugs 218 are proximal of blocks 214 and adjacent the side of cartridge 200 which is remote from base 34 when the cartridge is disposed in actuator 12. The distal facing surfaces of lugs 218 comprise additional stop surfaces 220 (FIG. 3). The surfaces of lugs 218 which face away from base 34 when cartridge 200 is disposed in actuator 12 are cam follower surfaces 222 (FIG. 3). The bottom portion of cartridge housing 204 defines a downwardly facing channel 224. The two laterally spaced inwardly facing side surfaces of channel 224 comprise alignment surfaces 226 (FIG. 12). The bottom surface of channel 224 comprises registration surface 228 (FIG. 3) which is perpendicular to the distal surface of cartridge 200.

Considering now the operation of the apparatus, the instrument is prepared for use by rotating knob 74 to retract cartridge holder 60 from distal frame leg 32 as shown in FIGS. 1 and 2. If anvil 110 is a removable and disposable member, as it is in the preferred embodiment, a new anvil is placed on leg 32. Then cartridge 200 is dropped into cartridge holder 60 in the manner depicted in sequential FIGS. 2, 3, and 4. The sides 62 and 64 of cartridge holder 60 are spaced apart by a distance greater than the thickness of cartridge 200 but less than the distance between the free ends of lugs 218 or the free surfaces of raised blocks 214. Accordingly, cartridge 200 drops relatively loosely into the open upper end of cartridge holder 60. Stop surfaces 216 pass along the distal end surfaces 68 of the sides 62, 64 of cartridge holder 60. Lugs 218, on the other hand, enter apertures 58 in the upper ends of side members 62, 64 (see especially FIG. 3). Leaf spring 210 contacts the base 66 of cartridge holder 60. The proximal portion of pin 208 (between spring 210 and the proximal head of the pin) enters slot 82 (FIG. 1) in the base 66 of cartridge holder 60.

It should be noted that during this phase of the insertion of cartridge 200 into cartridge holder 60, the cartridge is inserted along an axis which is distally inclined in the direction of cartridge insertion. The axis of cartridge insertion is therefore transverse to the longitudinal axis of distal frame leg 32. In addition, cartridge 200 is inclined so that it is substantially aligned with the axis of cartridge insertion. Leaf spring 210 must be deflected slightly toward cartridge housing 204 in order to cause lugs 218 to enter apertures 58.

Figure 4:
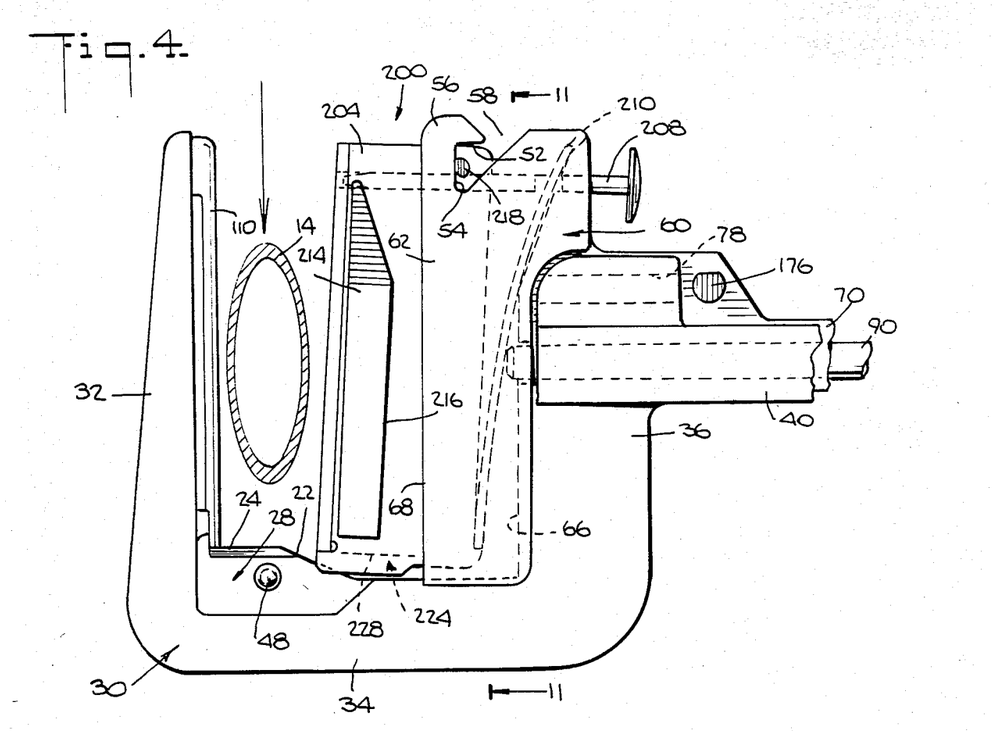
FIGS. 4–6 are views generally similar to FIG. 3 showing successive further stages in the operation of the apparatus.

Each of apertures 58 defines the proximal side of a hook-shaped structure 56 which projects upward from the associated side 62, 64 of cartridge holder 60. Each hook structure 56 defines a proximal facing stop surface 54 and a cam surface 52 which faces toward base 34. When lugs 218 begin to enter apertures 58 as shown in FIG. 3, a slight amount of downward manual pressure is applied to cartridge 200 to cause lugs 218 to pass around the proximal ends of hooks 56. When lugs 218 drop below cam surfaces 52, spring 210, which bears on the base 66 of cartridge holder 60, urges cartridge 200 in the distal direction until stop surfaces 220 on lugs 218 contact stop surfaces 54 on hooks 56 as shown in FIG. 4. Thus, once lugs 218 have passed under the proximal ends of hooks 56, spring 210 tends to urge cartridge 200 toward parallelism with anvil 110. Stop surfaces 54 and 220 cooperate to prevent cartridge 200 from moving distally relative to cartridge holder 60 any farther than is shown in FIG. 4. Cam surfaces 52, which are now above lugs 218, cooperate with lugs 218 to prevent cartridge 200 from being removed from cartridge holder 60 along an axis substantially parallel to leg 32. This prevents the cartridge from inadvertently falling out of the actuator.

At the same time that lugs 218 are passing the proximal ends of hooks 56, channel 224 on the bottom of cartridge 200 begins to engage a rail 28 which is formed on base 34. In particular, as shown in FIG. 4, a proximal portion of rail 28 enters a distal portion of channel 224 so that the side surfaces 226 of channel 224 contact the side surfaces 26 of rail 28. In contrast to the relatively loose fit between the sides of cartridge 200 and cartridge holder 60, the fit between the sides 226 of channel 224 and the sides 26 of rail 28 is relatively snug. This begins the process of precisely aligning cartridge 200 with anvil 110. The distal portion 24 of the top surface of rail 28 is perpendicular to anvil 110. The proximal portion of the top surface of rail 28 is inclined downward (away from cam surface 52) in the proximal direction.

The assembled instrument is now ready to receive the tissue 14 to be fastened. Tissue 14 is therefore positioned between the distal surface of cartridge 200 and anvil 110 as shown in FIG. 4.

Figure 5:
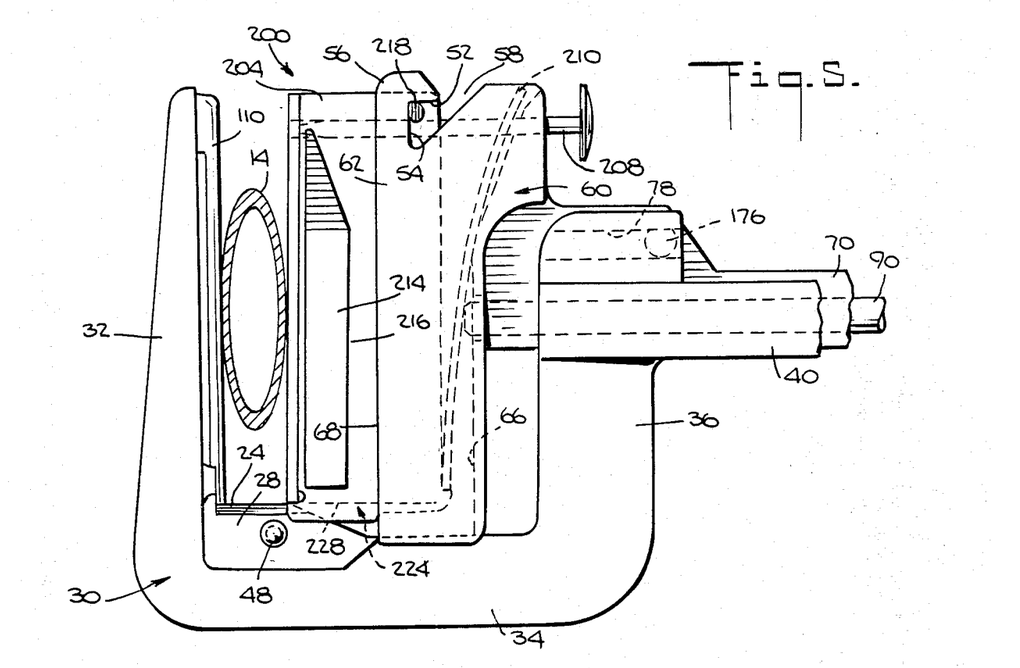

The next step in the operation of the instrument is to clamp tissue 14 between cartridge 200 and anvil 110. This is accomplished by rotating knob 74 to cause cartridge holder 60 to move in the distal direction toward anvil 110 as shown progressively in FIGS. 5-7. As cartridge holder 60 begins to move in the distal direction, spring 210 urges cartridge 200 to move distally with cartridge holder 60. Channel 224 therefore moves distally along rail 28. The bottom surface 228 of channel 224 eventually contacts the inclined top surface portion 22 of rail 28. Thereafter, continued distal motion of cartridge 200 causes the cartridge to shift upwardly in cartridge holder 60 until the bottom surface 228 of channel 224 reaches the portion 24 of the top surface of rail 28 which is perpendicular to anvil 110. This condition of the apparatus is shown in FIG. 5.

At about the time that surfaces 228 and 24 come into contact with one another, the cam follower surface portions 222 of lugs 218 contact cam surfaces 52 on hooks 56. Preferably, the distance between surfaces 24 and 52 is equal to or (most preferably) slightly less than the distance between surfaces 222 and 228, both of these distances being measured parallel to anvil 110. Thus when cam follower surface 222 comes into contact with cam surface 52, these surfaces cooperate to force surface 228 into firm contact with surface 24. This effect of surfaces 52 and 222 is enhanced as cartridge 200 gradually becomes more parallel with anvil 110 as described below. Because surface 24 is perpendicular to anvil 110, and because surface 228 is perpendicular to the distal surface of cartridge 200, firm contact between surfaces 24 and 228 provides the necessary registration between the staples 202 in cartridge 200 and the staple clinching depressions 112 in anvil 110.

Figure 6:
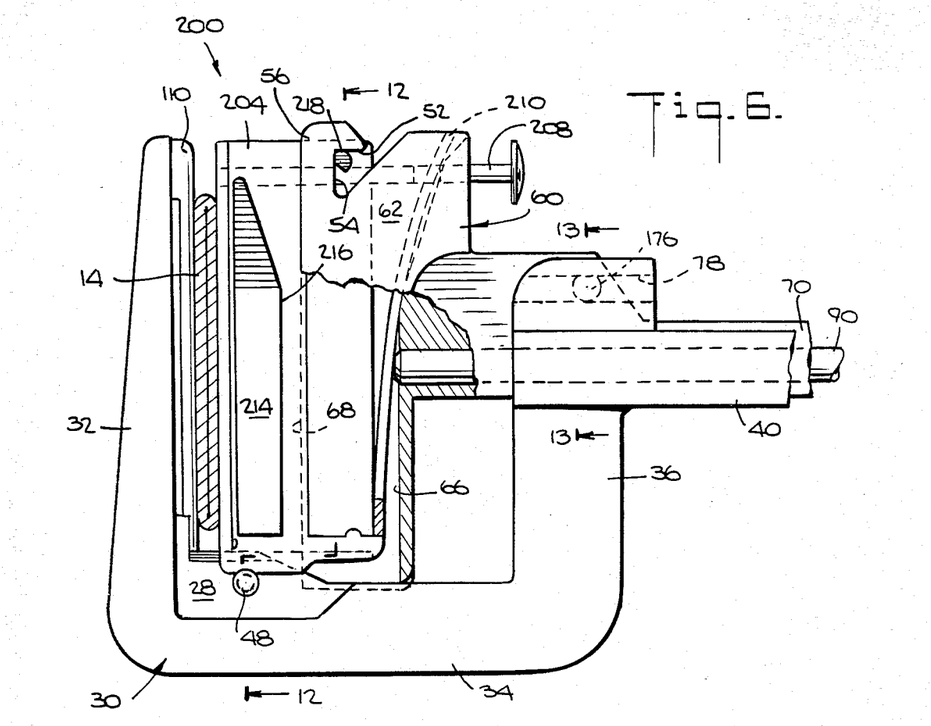
Figure 8:
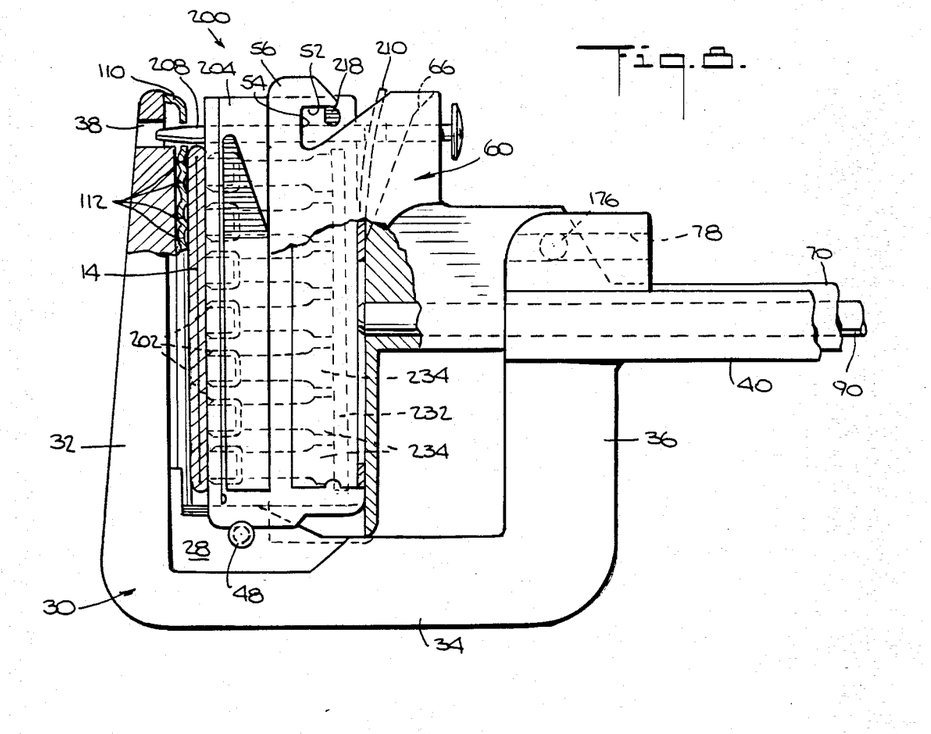
FIG. 8 is a view generally similar to FIGS. 3–6 showing the same condition of the apparatus as is shown in FIG. 7.

Continued rotation of knob 74 causes further distal motion of cartridge holder 60 as shown in FIG. 6 until the instrument reaches the condition shown in FIGS. 7 and 8, at which point the tissue is fully clamped and ready to be fastened. During the motion of cartridge holder 60 from the position shown in FIG. 5 to the position shown in FIGS. 7 and 8, cartridge 200 gradually clamps tissue 14 against anvil 110. As pressure is applied to tissue 14, spring 210 compresses against cartridge housing 204 and allows cartridge holder 60 to move distally relative to cartridge 200. This relative distal motion of cartridge holder 60 stops when stop surfaces 68 on the distal ends of cartridge holder sides 62 and 64 contact stop surfaces 216 on cartridge 200 as shown in FIGS. 7 and 8. Because stop surfaces 68 are parallel to anvil 110, and because stop surfaces 216 are parallel to the distal surface of cartridge 200, contact between surfaces 68 and 216 assures parallelism between anvil 110 and cartridge 200.

The above-described compression of spring 210 also causes alignment pin 208 to move distally relative to cartridge 200. Accordingly, the distal end of pin 208 automatically extends from cartridge 200 into aperture 38 in anvil 110 and distal frame leg 32 (see FIG. 8). This helps to align the ends of anvil 110 and cartridge 200 which are remote from base 34. The aligning action of pin 208 is enhanced by the presence of the proximal portion of pin 208 in slot 82 (FIG. 1) in the base 66 of cartridge holder 60. If anvil 110 is removable, the fact that alignment pin 208 must enter aperture 38 in anvil 110 also helps to assure registration of anvil 110 and cartridge 200.

The ends of elements 110 and 200 adjacent base 34 are aligned by contact between surfaces 26 and 226 as described in detail above. Headed pin 48, which, as shown in FIG. 12, extends just beyond the downwardly extending sides of channel 224, helps prevent deformation of these channel legs in the event that torque is applied to cartridge 200 about the longitudinal axis of anvil 110. This may be especially desirable if cartridge housing 204 is made of plastic.

It should be noted that during the above-described distal motion of cartridge holder 60 relative to cartridge 200, lugs 218 move along cam surfaces 52 (compare FIGS. 6 and 8). However, elements 52 and 218 remain in contact with one another, thereby continuing to assure firm contact between registration surfaces 24 and 228 and also preventing removal of cartridge 200 from holder 60.

Figure 9:
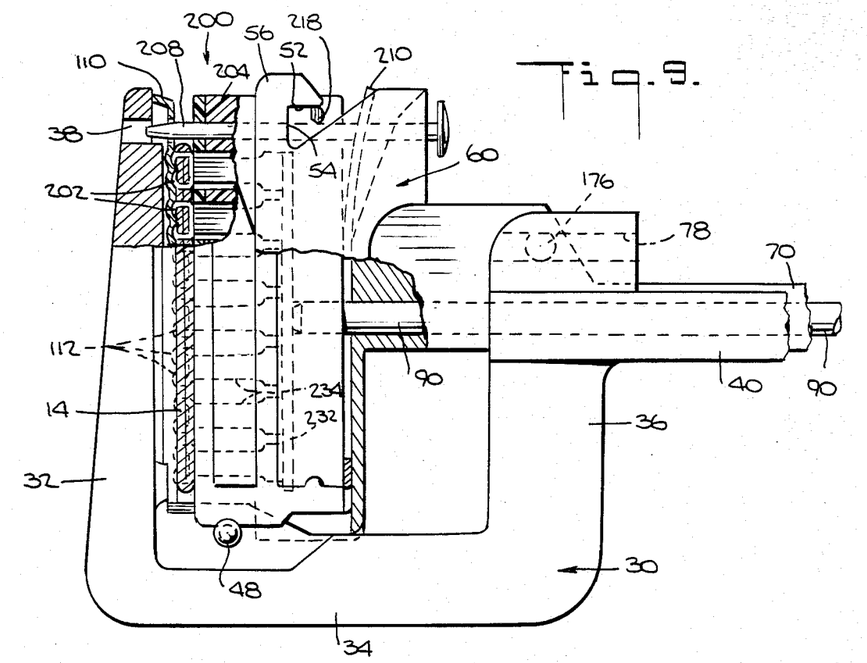
FIGS. 9 and 10 are views generally similar to FIGS. 3–6 and 8 showing successive further stages in the operation of the apparatus.

As mentioned above, when tissue 14 is fully clamped, handle projection 108 is adjacent notch 42 as shown in FIG. 7. This makes it possible to pivot handle 100 counter-clockwise as shown in broken lines in FIG. 7. When handle 100 is pivoted counter-clockwise, fastener pusher 90 moves in the distal direction relative to clamp actuator assembly 50, as shown in FIG. 9. The distal end of fastener pusher 90 passes through slot 230 (FIG. 1) in spring 210 and enters the proximal side of cartridge 200. There it contacts a transverse member 232 and drives that member in the distal direction. (If desired, the end of pusher 90 may be made T-shaped to help assure that transverse member 232 remains perpendicular to pusher 90 as member 232 moves distally.) Transverse member 232 in turn drives individual staple pushers 234 in the distal direction. Each individual staple pusher 234 is associated with a respective one of staples 202 so that pushers 234 drive all of staples 202 from cartridge 200. The legs of staples 202 pass through tissue 14, enter anvil depressions 112, and are thereby clinched or crimped to fasten the tissue as shown in FIG. 9. The travel of fastener pusher 90 is preferably limited by cooperation of lug 46 (FIG. 2) on frame 20 projecting into recess 92 in fastener pusher 90. This prevents overcompression of staples 202.

Figure 10:
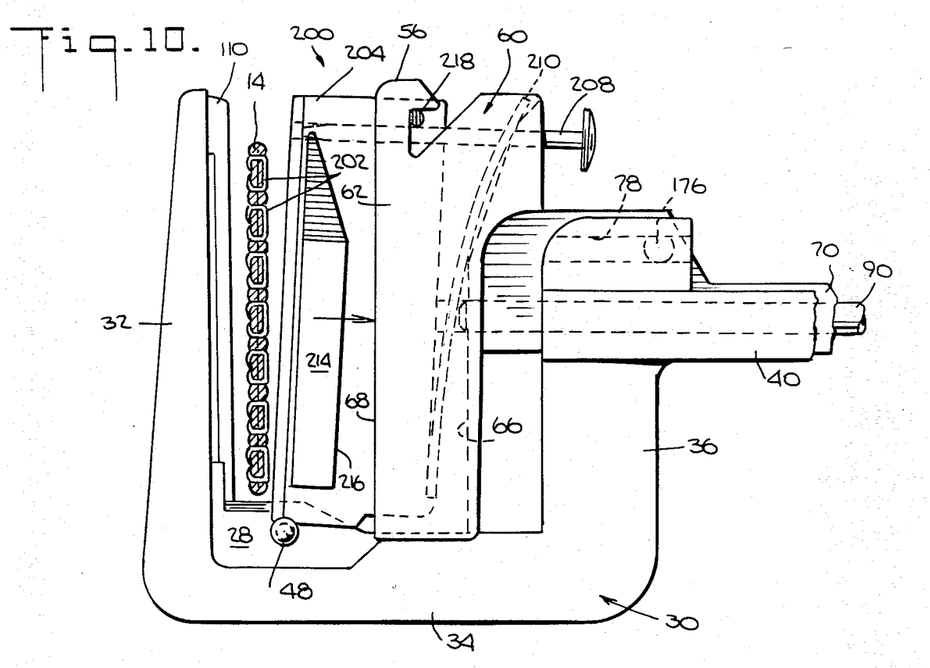

After staples 202 have been driven, handle 100 is released. Spring 106 restores handle 100 and fastener pusher 90 to their initial positions. The fastened tissue can be removed from the instrument by rotating knob 74 to retract cartridge holder 60 in the proximal direction as shown in FIG. 10. This also retracts cartridge 200, thereby relieving the clamping pressure on the tissue, and allowing spring 210 to flex away from cartridge housing 204. This in turn allows spring 210 to retract pin 208. The fastened tissue can then be removed from the instrument. In addition, cartridge 200 can be removed from actuator 12 by a manipulation which is the reverse of cartridge insertion.

Cartridge insertion and removal are quick and easy because cartridge 200 fits relatively loosely into cartridge holder 60. Precise alignment and registration of cartridge 200 and anvil 110 are achieved automatically after the cartridge has been inserted in actuator 12 (i.e., during operation of the actuator to clamp the tissue). In addition, substantially all of the elements which align and register cartridge 200 and anvil 110 are confined to the cartridge itself and elements of the actuator which are immediately adjacent to anvil 110 (i.e., rail 28 and aperture 38). This makes it possible to manufacture the remaining major portion of actuator 12 with less stringent tolerances, thereby reducing the initial cost of the actuator and making it easier and less expensive to maintain.

Another advantage of the disclosed apparatus is that alignment pin 208 is an integral part of cartridge 200. The operator of the instrument does not have to separately handle pin 208. Moreover, pin 208 operates automatically when the tissue is clamped in the instrument to perform its function of helping to align cartridge 200 and anvil 110.

Actuator 12 can be easily disassembled to facilitate cleaning. Pivot pin 104 can be disengaged by rotating knob 114 (FIG. 1). When pin 104 is disengaged, handle 100 can be removed from clamp actuator assembly 50. When clamp actuator assembly 50 is retracted sufficiently far in the proximal direction relative to frame 20, lugs 176 on clamp pusher 70 come out of longitudinal slots 78 (FIG. 3) in frame 20 as shown in FIG. 1. With handle 100 removed, frame 20 can be moved down relative to clamp actuator assembly 50 and completely separated from that assembly. Fastener pusher 90 will slide distally out of assembly 50 once frame 20 is removed. Knob 74 can also be removed from assembly 50. Actuator 12 is reassembled by reversing the foregoing procedure.

It will be understood that the foregoing is merely illustrative of the principles of the invention, and that various modifications can be made by those skilled in the art without departing from the scope and spirit of the invention. For example, two-part plastic surgical fasteners can be substituted for metal staples 202 as discussed in detail above.

I claim:

1. Surgical fastener applying apparatus comprising:
   a frame having a U-shaped distal portion;
   anvil means mounted on the distal leg of the U;
   cartridge holder means disposed in the U for linear reciprocal motion toward and away from the anvil means;
   cartridge means removably insertable in the cartridge holder means along an axis transverse to the distal leg of the U;
   first means associated with the cartridge means and the cartridge holder means for urging the cartridge means into parallel alignment with the anvil means when the cartridge holder means is reciprocated toward the anvil means; and
   second means associated with the cartridge means and the frame for causing the cartridge means to move in a direction substantially parallel to the distal leg of the U to bring the cartridge means into registration with the anvil means when the cartridge means is urged into parallel alignment with the anvil means.

2. The apparatus defined in claim 1 wherein the cartridge means fits loosely in the cartridge holder means prior to reciprocation of the cartridge holder means toward the anvil means.

3. The apparatus defined in claim 1 further comprising:
   third alignment means acting between the base of the U and an adjacent first end of the cartridge means for aligning the cartridge means and the anvil means in a direction perpendicular to the plane defined by the U when the cartridge means is inserted in the cartridge holder means.

4. The apparatus defined in claim 3 wherein the third alignment means comprises:
   a rail on a first one of the frame and the cartridge means, the longitudinal axis of the rail being parallel to the plane defined by the U; and
   a channel in a second one of the frame and the cartridge means, the longitudinal axis of the channel being parallel to the plane defined by the U, the rail being receivable in the channel so that the side surfaces of the rail slidably contact the side surfaces of the channel.

5. The apparatus defined in claim 3 further comprising:
   fourth alignment means acting between a second end of the cartridge means remote from the base of the U and an adjacent portion of the anvil means for further aligning the cartridge means and the anvil means in a direction perpendicular to the plane defined by the U when the cartridge holder means is reciprocated toward the anvil means.

6. The apparatus defined in claim 5 wherein the fourth alignment means comprises:
   an alignment pin mounted in the cartridge means for reciprocal motion parallel to the longitudinal axis of the pin, the longitudinal axis of the pin being substantially parallel to the base of the U when the cartridge means is inserted in the cartridge holder means;
   an aperture in the anvil means for receiving the distal end of the alignment pin; and
   means for reciprocating the alignment pin relative to the cartridge means toward the anvil means so that the distal end of the alignment pin enters the aperture when the cartridge holder means is reciprocated toward the anvil means.

7. The apparatus defined in claim 6 wherein the means for reciprocating the alignment pin comprises spring means connected between the cartridge means and the alignment pin, the spring means being deflected by contact with the cartridge holder means when the cartridge holder means is reciprocated toward the anvil means.

8. The apparatus defined in claim 5 wherein the second means comprises:
   a first registration surface on the base of the U and having a distal portion which is mutually perpendicular to the distal leg of the U and the plane defined by the U and a proximal portion which is inclined relative to the distal leg of the U and perpendicular to the plane defined by the U; and
   a second registration surface on the cartridge means adjacent the base of the U for slidably contacting the first registration surface when the cartridge means is inserted in the cartridge holder means.

9. The apparatus defined in claim 8 wherein the second means further comprises:
   cam and cam follower means associated with the cartridge means and the cartridge holder means for forcing the second registration surface against the first registration surface when the cartridge means is urged into parallel alignment with the anvil means.

10. The apparatus defined in claim 9 wherein the cartridge holder permits limited relative movement of the cartridge means parallel to the base of the U even after insertion of the cartridge means in the cartridge holder.

11. The apparatus defined in claim 10 further comprising first stop means acting between the cartridge means and the cartridge holder means for stopping distal motion of the cartridge holder means relative to the cartridge means, the first stop means aligning the cartridge means parallel to the anvil means when the first stop means is engaged.

12. The apparatus defined in claim 11 further comprising second stop means acting between the cartridge means and the cartridge holder means for stopping distal motion of the cartridge means relative to the cartridge holder means.

13. The apparatus defined in claim 12 further comprising spring means acting between the cartridge holder means and the cartridge means for resiliently urging the cartridge means toward parallelism with the anvil means after the cartridge means has been inserted into the cartridge holder means.

14. The apparatus defined in claim 13 further comprising means for preventing removal of the cartridge means from the cartridge holder means along an axis substantially parallel to the distal leg of the U.

15. The apparatus defined in claim 13 wherein the first means for urging the cartridge means into substantially parallel alignment with the anvil means acts on the cartridge means through the spring means.

16. The apparatus defined in claim 1 further comprising spring means acting between the cartridge holder means and the cartridge means for resiliently urging the cartridge means toward parallelism with the anvil means after the cartridge means has been inserted into the cartridge holder means.

17. The apparatus defined in claim 16 further comprising means for preventing removal of the cartridge means from the cartridge holder means along an axis substantially parallel to the distal leg of the U.

18. The apparatus defined in claim 1 further comprising:
   means mounted on the frame for driving the surgical fasteners from the cartridge; and
   means for inhibiting operation of the means for driving the surgical fasteners unless the cartridge holder means has been reciprocated toward the anvil means by at least a predetermined amount.

19. The apparatus defined in claim 18 wherein the means for inhibiting is visible to the user of the apparatus and provides a visible indication of the amount of reciprocation of the cartridge holder means.

* * * * *